United States Patent [19]

Duh et al.

[11] Patent Number: 5,151,086
[45] Date of Patent: Sep. 29, 1992

[54] LAPAROSCOPIC TUBE PLACEMENT METHOD

[75] Inventors: Quan-Yang Duh; Lawrence W. Way, both of San Francisco, Calif.

[73] Assignee: The Regents of the University of California, Oakland, Calif.

[21] Appl. No.: 780,773

[22] Filed: Oct. 22, 1991

[51] Int. Cl.⁵ ............................................. A61M 31/00
[52] U.S. Cl. ......................................... 604/51; 604/96
[58] Field of Search ............................ 604/51, 49, 96

[56] References Cited

U.S. PATENT DOCUMENTS

| | | | |
|---|---|---|---|
| 3,920,023 | 11/1975 | Dye et al. | 604/51 |
| 3,961,632 | 6/1976 | Moossun . | |
| 4,235,238 | 11/1980 | Ogiu et al. . | |
| 4,669,473 | 6/1987 | Richards et al. . | |
| 4,705,040 | 11/1987 | Mueller et al. | 604/51 |
| 4,798,592 | 1/1989 | Parks | 604/49 |
| 4,813,929 | 3/1989 | Semrad | 604/51 |
| 5,002,557 | 3/1991 | Hasson . | |
| 5,006,106 | 4/1991 | Angelchik . | |
| 5,037,387 | 8/1991 | Quinn et al. | 604/51 |
| 5,041,129 | 8/1991 | Hayhurst et al. . | |

OTHER PUBLICATIONS

Russian Publication (with translation)—Cherenkov, V. G. and Butenko, A. T.; "Laparoscopic Methods for Creating Fistulae in Cancer of the Digestive Organs"; Department of Oncology, Semipalatinsk Medical Institute; Jun. 20, 1983; pp. 41–45.

Russian Publication (with translation)—Prudkov, I. D. and Torsyan, R. T.; "Laparoscopic Operations on the Stomach"; Clinic of General Surgery, Sverdlovsk Medical Institute; *Vestnik khirurgii,* vol. 12, 1984; pp. 16–19.

Cope, C.; "Suture Anchor for Visceral Drainage"; *AJR,* vol. 146; Jan. 1986; pp. 160–162.

*Primary Examiner*—Paul J. Hirsch
*Attorney, Agent, or Firm*—Majestic, Parsons, Siebert & Hsue

[57] ABSTRACT

A method of placing a tube through a body wall into a hollow body organ is provided. The method includes performing a laparoscopy, inserting a plurality of retraction device introducers through the body wall, fixing a like plurality of retraction devices to the body wall by means of the retraction device introducers, fixing the body organ to the interior surface of the body wall and inserting a tube through the body wall into the organ; and fixing the tube to the organ. In two applications, the method may be used with gastrostomy or jejunostomy.

15 Claims, 2 Drawing Sheets

LAPAROSCOPIC TUBE PLACEMENT METHOD

FIELD OF THE INVENTION

This invention relates to a laparoscopic method of placing a tube in a hollow body organ through a body wall. More specifically, it relates to laparoscopic placing of a feeding tube in the stomach by means of a gastrostomy or in the small intestine by means of a jejunostomy.

BACKGROUND OF THE INVENTION

Long term external feeding of debilitated patients is perhaps best accomplished by means of a gastrostomy or a jejunostomy. As between the two, feeding through the stomach by means of a gastrostomy is easier than through the jejunum portion of the small intestine by means of a jejunostomy. This is because the stomach provides a reservoir for bolus feeding. There is also less chance of encountering problems with osmotic diarrhea. Some indications for gastrostomy are when a patient requires feeding, or venting an obstructed stomach.

Either of these procedures can be performed by conventional surgical techniques, i.e. open surgery. However, the invasiveness and trauma of such open procedures are well known. To avoid some of the problems inherent with open gastrostomy, a percutaneous endoscopic gastrostomy procedure has been developed. With the percutaneous endoscopic gastrostomy procedure, an endoscope is placed down the esophagus into the stomach interior. The endoscope is used to view the interior wall of the stomach as the introducer is inserted through the exterior body wall. Similarly, viewing of the interior wall of the stomach also facilitates placement of a tube by means of a tube introducer. While the interior stomach wall is thus viewed, the tube introducer is directly viewed in the stomach, but not in the peritoneal cavity.

In some situations, however, percutaneous endoscopic gastrostomy cannot be done. One such situation is where the patient needs a gastrostomy, but cannot undergo or has failed one due to an obstruction in the esophagus, e.g. because of pharyngeal or esophageal cancer. Another situation is where an endoscopist is not available. Still another is with patients with gastroesophageal reflux or a history of aspiration pneumonia. With these latter patients, a jejunostomy may be indicated. However, jejunostomy performed by using a technique similar to percutaneous endoscopic gastrostomy is not satisfactory because of the high complication rate. Accordingly, jejunostomy is traditionally placed by means of a laparotomy.

Attempts have also been made to perform jejunostomy laparoscopically using long needles carrying sutures through the body wall. See: Regan and Scarrow, "Laparoscopic Jejunostomy," *Endoscopy*, 1990, pp. 39-40. A needle holder, also passed through the body wall, is then manipulated to suture the jejunum to the abdominal wall and to pass the needles up through the body wall again. This procedure has disadvantages. Overall, the procedure is very difficult and time-consuming, especially when the body wall is thick. It requires a difficult technique of endoscopically-directed suturing of the small intestine and the abdominal wall using a long, straight needle. It also requires making another opening in the body wall to admit the needle holder. Still further, the feeding tube is placed through a stab wound, which may be large and less controlled.

SUMMARY AND OBJECTS OF THE INVENTION

It is the primary object of this invention to provide a method for placing a tube in a hollow organ through the exterior body wall that does not have the problems encountered with previous surgical methods.

It is a further object to provide such a method of tube placement where the surgical site for placement of the tube on the body organ is in direct view.

It is a still further object of this invention to provide such a method that does not require access through the patient's esophagus.

It is a still further object to provide such a method using laparoscopy to take advantage of situations where laparoscopy is currently being performed, such as with an abdominal exploration or a biopsy.

It is a further object to provide such a method which improves access to hollow organs by insufflation of the organ by air.

It is a still further object to provide a laparoscopic method for gastrostomy or jejunostomy.

The inventive method broadly comprises performing a laparoscopy in a location through the exterior body wall to give access to the body organ. A plurality of retraction device introducers are then inserted through the body exterior wall. A like plurality of retraction devices are then fixed to the body organ by means of the introducers.

Parenthetically, the retraction devices may conveniently be "T" fasteners as disclosed and claimed in U.S. Pat. No. 4,705,040. The disclosure of said patent is hereby incorporated by reference. The incorporated patent discloses a hollow, slotted needle in the form of an introducer carrying a retaining device in the form of a T-fastener retraction device attached to a tension filament or suture. The T-fastener is adapted to be released from the introducer after the needle has penetrated a hollow organ. The organ is fixed by adjusting the tension on the filament outside the body by means bearing upon the exterior of the body including a pledgette and a washer.

The body organ is then fixed to the interior surface of the exterior body wall by means of the retraction devices. Finally, a tube is inserted through the body wall and into the organ. To do this, a tube introducer such as a J-Guidewire is first introduced through the body wall. A tube having a balloon thereon is passed over the tube introducer and into the organ. Alternatively, a hollow peel-away introducer can be used, and the tube is passed inside the introducer and into the organ. The balloon is then inflated and the tube introducer removed from the body. Alternatively, if the tube does not include a balloon, the tube may be fixed by suturing.

The inventive method using laparoscopy has several advantages in addition to being less invasive. These are: diminished narcotic requirement; decreased total cost; earlier enteral feeding; and improved cosmetic appearance. Further, the procedure uses a tube introducer and a dilator, which produces a smaller and more controlled hole for admission of the tube.

Further and other objects and advantages will become more readily apparent from a review of the following description and claims.

DETAILED DESCRIPTION

Turning to the drawings, the inventive method will now be described. The method is generally applicable to a hollow body organ located within a body cavity. For sake of illustration, the method will be described by having reference to the stomach and performing a laparoscopic gastrostomy. The laparoscopic gastrostomy is performed as follows:

Selecting and Preparing the Gastrostomy site.

Figure 1:
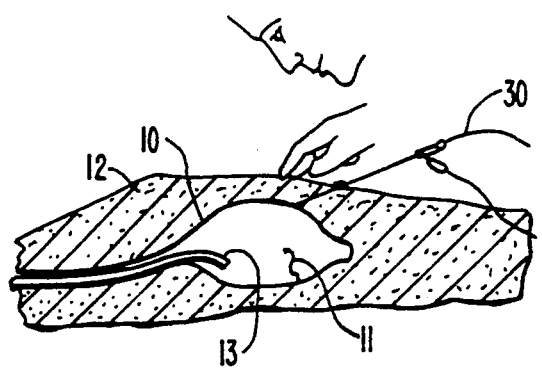
FIG. 1 is a side elevation partial view of a body showing the step of determining the locations of the gastrostomy site.

Preoperative preparation will include placement of a nasogastric tube (optional), endotracheal intubation, ventilation, and induction of anesthesia as usual for laparoscopic surgery. The peritoneum is then insufflated at 15 mmHg with a Veress needle after confirmation of correct placement by needle aspiration or injection of 10 cc of Saline. Bloody aspirate, injection requiring excessive pressure, or asymmetric distention of the abdomen upon insufflation may indicate the needle is not in the proper position. If incorrect placement is confirmed, the needle is removed and a different site is selected. Next, the trocar is placed subumbilically. A laparoscope is inserted and a diagnostic laparoscopy is performed. The stomach is insufflated via a nasogastric tube to improve gastric access. The abdominal contents are identified laparoscopically, ascertaining the accessibility of the stomach. If the stomach is obscured by bowel, one or two 5 mm laparoscopic trocars are inserted through the abdominal wall to insert graspers through. The graspers are manipulated to bring the stomach into view in order to place the gastrostomy tube. The locations of the gastrostomy site are determined externally on the abdominal wall 10 and internally on the anterior gastric wall 12 by finger depression viewed laparoscopically, as shown in FIG. 1. The nasogastric tube is shown in this Figure at 13.

Placing the T-Fasteners.

Figure 2:
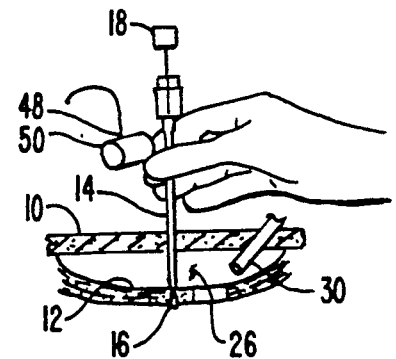
FIG. 2 is a side elevation view of a portion of a body wall showing a T-fastener retraction device being inserted through the body wall and gastric wall by means of a retraction device introducer in the form of a slotted needle.

One to two 5 mm laparoscopic trocars are inserted, if needed, through the upper abdominal wall to provide access for graspers to hold the stomach 11 while placing the T-fasteners. If the stomach is obscured by bowel, graspers are utilized to bring the stomach 11 into view in order to place the gastrostomy tube. The center of the 2×2 gauze is placed over the insertion site. The T-fasteners are inserted at the midpoint of each side of the 2×2 gauze. A slotted needle with a T-fastener is preloaded, and the white grommet checked. It should be positioned at the end of the stylet. The pneumoperitoneum is decreased to 7-10 mmHg which will allow the stomach to be drawn up to the anterior abdominal wall. The preloaded slotted needle is inserted with a gentle but firm thrust through the most cephalad of the four T-fastener sites. The needle 14 with the loaded T-fastener 16 is inserted through the gastric wall as shown in FIG. 2 using the graspers to stabilize the stomach if needed. This is done under direct vision by laparoscopy so that the needle does not accidentally penetrate other body organs.

Figure 3:
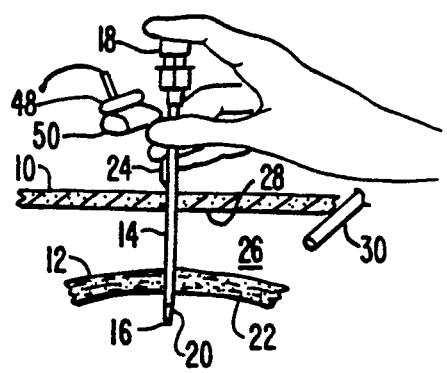
FIG. 3 is a side elevation view of the same showing the introducer needle advanced beyond the stomach wall.

When the needle has advanced beyond the gastric mucosal surface, the resistance drops and the stomach wall is no longer depressed by the needle. If the needle has not penetrated the gastric mucosa, the "T" will not advance. The white grommet 18 on the stylet is tapped to dislodge the T-fastener 16 from the slot, as shown in FIG. 3. The needle 14 and stylet 20 are withdrawn simultaneously, while continuing to gently pull the T-fastener 16 until it is adhered to the gastric mucosa 22. The tension of the suture 24 is an indication that the T-fastener 16 is pulled against the gastric mucosa 22. If the T-fastener is accidentally dislodged into the peritoneum 26, it can be retrieved using a grasper. Tension is kept on the T-fastener while pulling it up toward the anterior abdominal wall until the T-fastener has deformed the stomach wall upwards. Some distance should be kept between the stomach wall and the anterior abdominal wall 28 so each subsequent T-fastener can be placed under direct vision through the laparoscope 30. Pulling the T-fastener snug against the abdominal wall at this point in the procedure will diminish the visualization required to place the T-fasteners. This process is repeated for the other three T-fasteners, starting with the ones near the lesser curvature of the stomach and ending with the ones near the greater curvature. After all four T-fasteners are properly positioned in a square pattern, the sutures are pulled to snugly fix the anterior wall 12 of the stomach to the anterior abdominal wall 28. An assistant should hold the T-fasteners or the clamps holding the T-fasteners while creating the stoma tract and inserting the gastrostomy tube, as will be described hereinafter.

Creating the Stoma Tract.

Figure 4:
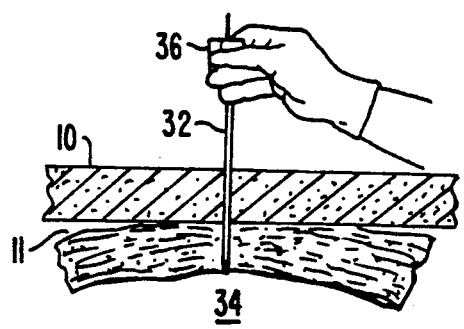
FIG. 4 is an enlarged side elevation view of the same showing the stomach wall pulled into contact with the abdominal wall by pulling on the retraction device.
Figure 5:
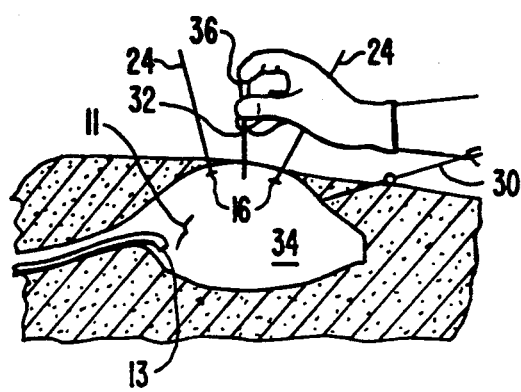
FIG. 5 is a side elevation view similar to FIG. 1 showing the stomach adhered to the abdominal wall and a needle in place for passing the J-Guidewire.

As seen in FIGS. 4 and 5, with the stomach adhered to the abdominal wall, an 18 Ga nonslotted needle 32 is inserted percutaneously into the gastric lumen 34. The best angle of insertion is perpendicular to the surface of the skin. To minimize loss of air through the needle, the needle hub 36 is covered with a finger, as shown in the subject figures, or by a syringe.

Figure 6:
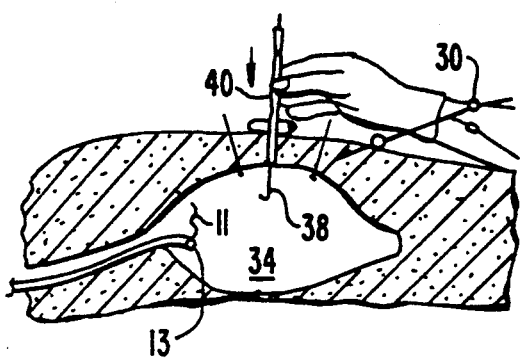
FIG. 6 is a view of the same showing the dilator passed over the J-Guidewire through the abdominal wall and into the lumen of the stomach and the stomach wall dropped away from the abdominal wall.
Figure 7:
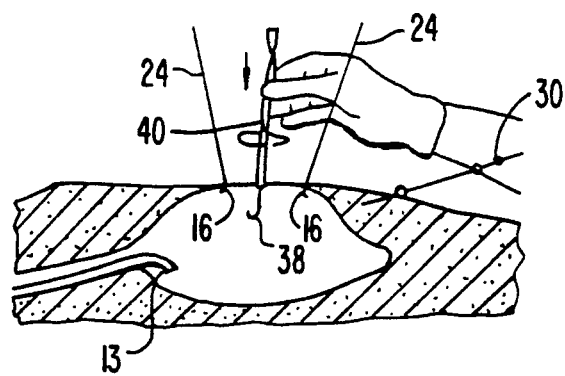
FIG. 7 is a view of the same showing the use of a larger dilator over a J-Guidewire tube introducer, and the stomach adhered to the abdominal wall.

As shown in FIG. 6, J-Guidewire 38 is passed through the 18 Ga needle 32 into the gastric lumen 34, and then the 18 Ga needle is withdrawn and discarded, leaving the J-Guidewire in place. The stomach is dropped as shown by loosening the T-fasteners 16 slightly to validate that the J-Guidewire 38 is in the stomach. then the assistant retightens the T-fasteners to adhere the stomach snugly to the abdominal wall. A scalpel blade is used to create a small skin incision that extends alongside the J-Guidewire, downward through the subcutaneous layer and the fascia of the abdominal musculature. In the subsequent steps that require use of the J-Guidewire, care should be taken not to pull up on the J-Guidewire and dislodge it. Care should be taken during dilating to stay perpendicular to the skin so that the J-Guidewire will not become kinked. After lubricating the outside surface of the smallest of a series of dilators 40 with a water-soluble lubricant, it is passed over the J-Guidewire and a gentle but firm downward, to-and-fro motion in the arrow direction is used to create a tract into the gastric lumen, as shown in FIG. 7. The dilator is then withdrawn, being careful not to dislodge the J-Guidewire. The steps are then repeated using progressively larger dilators in the series, until a 22 French stoma has been created.

Inserting the Gastrostomy Tube.

Figure 8:
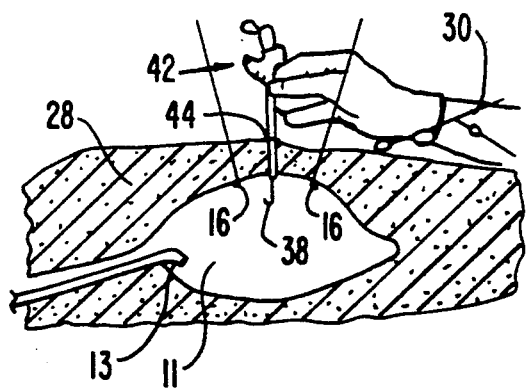
FIG. 8 is a view of the same showing the placement of a gastrostomy tube over the J-Guidewire introducer.
Figure 9:
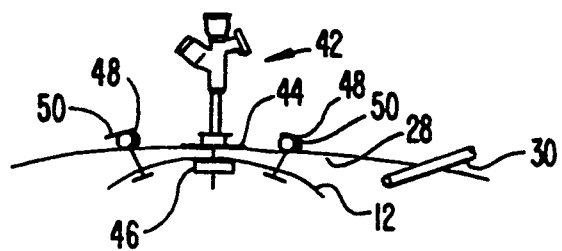
FIG. 9 is a side elevation view of a part of a body wall showing the gastrostomy tube fully in place and the retraction devices in place fixing the stomach to the abdominal wall.

The gastrostomy tube 42 is prepared by sliding the skin disc 44 to the upper part of the tube. After lubricating the tip of the stylet with water-soluble lubricant, the stylet is inserted into the gastrostomy tube. The hub of the stylet is securely placed into the feeding port of the tube. The tapered distal tip of the stylet should protrude from the tube's distal feeding port. After lubricating the outside surface of the gastrostomy tube with the water-soluble lubricant, the stylet-stiffened tube is passed over the J-Guidewire and a gentle but firm downward, to-and-fro motion is used to insert the tube into the gastric lumen. The balloon 46 on the gastrostomy tube is filled with 15 cc of sterile water or saline. Air should not be used to fill the balloon. The stomach is dropped away from the anterior abdominal wall 28 by loosening the T-fasteners 16, as shown in FIG. 8, to confirm laparoscopically that the entire balloon is inside the stomach. After visual confirmation of appropriate tube placement, the T-fasteners are retightened to pull the stomach back up snugly against the abdominal wall. Each T-fastener is stabilized by sliding the nylon washer 48 down against the pledget 50, and crimping the aluminum crimps with a clamp such as a hemostat (not shown) to hold the T-fastener in position. Any excess suture is cut off. The J-Guidewire is withdrawn with the stylet. Allowing for slight in-and-out play of the tube, the skin disc 44 is slid down the tube and snugged gently against the skin of the abdominal wall 10.

The gastrostomy tube feeding port can be tested by injecting saline through it. The laparoscopist should ensure that there is no leakage around the site. The pneumoperitoneum is deflated and then the laparoscope and nasogastric tube are removed. After ten days to two weeks, the stomach is usually well attached to the anterior abdominal wall. The sutures for the four T-fasteners can be cut at skin level, allowing the 1-cm stainless steel "T" to pass into the stomach and bowel.

The method of laparoscopy jejunostomy is similar to that of laparoscopic gastrostomy. Before the laparoscopy step is performed, however, the proximal jejunum is identified by one or more of the following techniques: (1) change the patient's position (e.g., reverse Trendelenburg); (2) insert additional trocars, if needed, for additional graspers to lift the omentum and transverse colon away from the proximal jejunum; (3) intubate and insufflate the stomach and proximal jejunum, if possible; and (4) place a long endoscope into the proximal jejunum, if necessary.

Air can be introduced into the jejunum through the needle introducer of the first T-fastener. This facilitates placement of the remaining T-fasteners and avoids accidental penetration of the posterior wall. The tip of the jejunostomy tube should be placed about 6 to 10 cm beyond the jejunostomy and the tube should be directed distally. It should be secured to the skin. Alternatively, the tube may be fixed by means of an intraluminal balloon. A low profile balloon, e.g. disc shape, should be used. Contrast media may be injected into the jejunostomy tube to confirm correct placement and that no leakage has occurred. The placement of the jejunostomy tube can be done either over a stiff introducer or inside a peel-away hollow introducer.

It is to be understood that while the invention has been described above in conjunction with the preferred specific embodiments, the description and examples are intended to illustrate and not limit the scope of the invention, which is defined by the scope of the appended claims.

What is claimed is:

1. A method of placing a tube in a hollow body organ through a body wall having an interior surface juxtaposed with the body organ and separated therefrom by a space and an exterior surface outside the body comprising the steps of:
   (a) performing a laparoscopy through the body wall in a location so as to bring the organ under direct vision;
   (b) inserting a plurality of retraction device introducers through said body wall and into said space and into said organ under direct vision;
   (c) fixing a like plurality of retraction devices to said organ by means of said introducers;
   (d) fixing said body organ in contacting relation with said interior surface by means of said retraction devices;
   (e) inserting a hollow tube through said body wall into said body organ; and
   (f) fixing said tube in said body organ.

2. The method of claim 1 wherein step (e) of said claim comprises:
   (a) inserting a tube introducer through said body wall and into said organ;
   (b) passing a tube having a balloon thereon over said tube introducer until said balloon is within said hollow organ.

3. The method of claim 2 wherein step (f) of claim 1 comprises the steps of:
   (a) inflating said balloon so as to fix said tube within said organ; and
   (b) withdrawing said tube introducer from said body.

4. The method of claim 2 wherein said tube introducer forms a hole in said body wall and further including the step of enlarging said hole by means of a first dilator.

5. The method of claim 4 further including the steps of using a series of progressively larger dilators to progressively enlarge said hole.

6. The method of claim 1 including the step of withdrawing said retraction device introducers from said body after the step of fixing said retraction devices to said organ.

7. The method of claim 1 including the step of insufflating the body organ prior to the step of fixing said plurality of retraction devices thereto.

8. The method of claim 1 further including the withdrawal of said tube introducer from said body.

9. The method of claim 1 wherein the body organ is the stomach, the body wall is the abdominal wall, and the space is the peritoneum, whereby a gastrostomy is performed.

10. The method of claim 1 wherein the body organ is the small intestine.

11. The method of claim 10 wherein the hollow tube is inserted into the jejunum portion of the small intestine, whereby a jejunostomy is performed.

12. The method of claim 1 wherein said retraction device introducers are slotted needles and wherein said retracton devices are T-fasteners.

13. The method of claim 2 wherein said tube introducer is a J-Guidewire.

14. The method of claim 2 wherein said tube introducer is a peel-away, hollow introducer.

15. A method of placing a tube in a hollow body organ through a body wall having an interior surface and an exterior surface comprising the steps of:
(a) performing a laparoscopy through the body wall in a location so as to bring the organ under direct vision;
(b) inserting a plurality of retraction device introducers through the body wall;
(c) fixing a plurality of retraction devices to said organ by means of said introducers;
(d) fastening said body organ to said interior surface by means of said retraction devices;
(e) inserting a tube introducer through said body wall and into said organ;
(f) passing a tube having a balloon thereon over said tube introducer until said balloon is within said organ;
(g) inflating said balloon to fix said tube in said organ; and
(h) withdrawing said tube introducer from said body.

* * * * *